United States Patent [19]

Brändström et al.

[11] 3,998,790

[45] Dec. 21, 1976

[54] PHENOXY-HYDROXYPROPYLAMINES, THEIR PREPARATION, AND METHOD AND PHARMACEUTICAL PREPARATIONS FOR TREATING CARDIOVASCULAR DISEASES

[75] Inventors: Arne Elof Brändström; Per Arvid Emil Carlsson, both of Goteborg; Stig Ake Ingemar Carlsson, Molnlycke; Hans Rudolf Corrodi, Sodertalje; Lars Ek, Onsala; Bengt Arne Hjalmar Ablad, Goteborg, all of Sweden

[73] Assignee: Aktiebolaget Hassle, Goteborg, Sweden

[22] Filed: Jan. 15, 1974

[21] Appl. No.: 433,451

Related U.S. Application Data

[60] Division of Ser. No. 342,749, March 19, 1973, Pat. No. 3,873,600, and a continuation-in-part of Ser. No. 115,851, Feb. 16, 1971, abandoned.

[52] U.S. Cl. .................. 260/570.7; 260/307 C; 260/348 R; 260/471 C; 260/501.17; 260/501.19; 260/516; 260/521 R; 260/553 A; 260/570.9; 260/544 N; 424/300; 424/316; 424/330

[51] Int. Cl.$^2$ ..................................... C07C 93/06

[58] Field of Search .............. 260/501.17, 501.19, 260/570.7

[56] References Cited

UNITED STATES PATENTS

| | | | |
|---|---|---|---|
| 3,203,992 | 8/1965 | Kunz et al. | 260/570.7 |
| 3,541,130 | 11/1970 | Koppe et al. | 260/570.7 X |
| 3,631,108 | 12/1971 | Brändström et al. | 260/570.7 |
| 3,755,413 | 8/1973 | Koppa et al. | 260/570.7 |

OTHER PUBLICATIONS

Ciba, "Chemical Abstracts", vol. 66, p. 6129. (1967).

*Primary Examiner* — Robert V. Hines
*Attorney, Agent, or Firm* — Brumbaugh, Graves, Donohue & Raymond

[57] ABSTRACT

Para-substituted phenoxy-hydroxypropylamines having the general formula

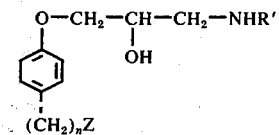

and pharmaceutically acceptable, non-toxic acid addition salts thereof, wherein R' is an isopropyl or tertiarybutyl radical; Z is a member selected from the group consisting of -OR", -SR", and -NHCOOR", R" being a straight or branched lower alkyl radical having 1 to 3 carbon atoms; and n is 1, 2, or 3, are disclosed as are methods for their preparation. Pharmaceutical preparations are prepared whose active ingredients include at least one of the newly discovered phenoxy-hydroxypropylamine compounds. Therapeutically effective doses of these preparations selectively block the β-receptors of the heart making them useful in treating heart diseases in animals including humans.

20 Claims, No Drawings

PHENOXY-HYDROXYPROPYLAMINES, THEIR PREPARATION, AND METHOD AND PHARMACEUTICAL PREPARATIONS FOR TREATING CARDIOVASCULAR DISEASES

This is a division, of application Ser. No. 342,749, filed Mar. 19, 1973 and now U.S. Pat. No. 3,873,600, and this is a continuation-in-part of our copending application Ser. No. 115,851 filed Feb. 16, 1971 and now abandoned.

The present invention relates to phenoxy-hydroxypropylamines and, in particular, to para-substituted phenoxy-hydroxypropylamines and methods for their preparation. The invention also relates to the preparation of pharmaceutical preparations containing such para-substituted phenoxyhydroxypropylamines as active ingredients and to a method for the pharmacological use of such compounds.

$\beta$-Receptor blocking agents such as propranolol,

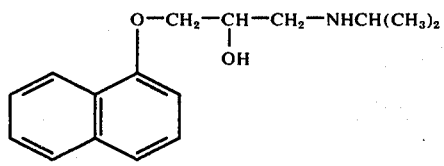

alprenolol,

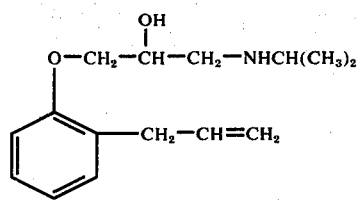

and oxprenolol,

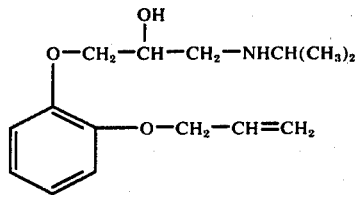

have been shown to possess good therapeutic effects in treating heart diseases and vascular diseases, such as angina pectoris, hypertension, vasoregulatoric neurasteni and certain forms of arrythmia.

certain disadvantages have been experienced in the therapeutic use of these compounds since they block not only the $\beta$-receptors of the heart, which leads to the therapeutic effect, but also the $\beta$-receptors in blood vessels and bronchi. The latter blocking activity results in undesired side effects with some patients having manifest or latent asthma. Blocking of the $\beta$-receptors in the bronchi may in such cases lead to bronchospasm and attacks of asthma. For this reason, asthma is a contraindication for heart disease treatment with the known $\beta$-receptor-blocking substances such as propanolol, alprenolol, and oxprenolol. The receptor blocking effect on blood vessels of these compounds causes adrenaline, which is released from the marrow of the suprarenal glands, to have a pure pressor effect instead of the balanced pressor-depressor effect normally maintained by adrenaline flow.

Accordingly, the main object of the invention is to provide new para-substituted phenoxy-hydroxypropylamine compounds having variable pharmacological properties which can be used in the treatment of heart diseases.

Another object of this invention is to provide new compounds which have a therapeutic effect in treating heart diseases without inducing complications due to $\beta$-blockade in bronchi and in blood vessels.

These and other closely related purposes of the present invention are achieved by administering para-substituted phenoxyhydroxypropylamine derivatives characterized by the following general formula:

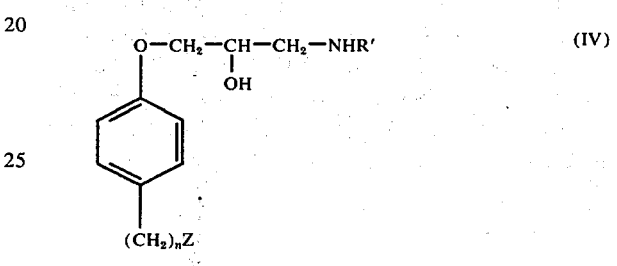

and pharmaceutically acceptable, non-toxic acid addition salts thereof, wherein R' is an isopropyl or tertiarybuty radical; Z is a member selected from the group consisting essentially of -OR'', -SR'', and -NHCOOR'', R'' being a straight or branched chain lower alkyl radical having 1 to 3 carbon atoms; and n is 1, 2, or 3.

The para-substituted phenoxy-hydroxypropylamine compounds discovered contain an asymmetric carbon atom and, therefore, they exist as optically active forms. The racemic mixture can, of course, be resolved into its optical antipodes by well known methods, such as by using optically active acids such as tartaric acid, camphor-10-sulphonic acid, dibenzoyl tartaric acid, and the like. Some examples of compounds according to the invention are: 1-isopropylamino-3-[p-($\beta$-methoxyethyl)-phenoxy]-propanol-2; 1-isopropylamino-3-[p-($\beta$-ethoxyethyl)-phenoxy]-propanol-2; 1-isopropylamino-3-[p-(ethoxymethyl)-phenoxy]-propanol-2; 1-isopropylamino-3-[p-($\gamma$-methoxypropyl)-phenoxy]-propanol-2; 1-isopropylamino-3-[p-($\beta$-methylmercaptoethyl)-phenoxy]-propanol-2; and 1-isopropylamino-3-[p-($\beta$-methoxycarbonylamidoethyl)-phenoxy]-propanol-2.

1-Isopropylamino-3-[p-($\beta$-methoxyethyl)-phenoxy]-propanol-2 and 1-isopropylamino-3-[p-($\beta$-methoxycarbonylamidoethyl)-phenoxy]-propanol-2 are preferred both as racemates as well as in the form of their pharmacologically and optically active isomers.

The para-substituted phenoxy-hydroxypropylamines of Formula IV may be prepared by several methods which are defined as follows:

A. Reacting a compound of the formula

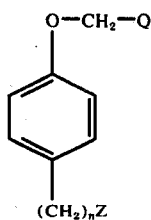
(V)

with a compound of the formula

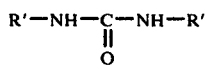
(VI)

in which formulas R' is an isopropyl or tertiary-butyl radical; Z is a member selected from the group consisting of -OR'', -SR'', and -NHCOOR'', R'' being a straight or branched lower alkyl radical having 1 to 3 carbon atoms; and n is 1, 2, or 3. Q in Formula V represents

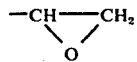

or -CHOH-CH$_2$-X, wherein X is a halogen atoms, preferably chlorine.

B. Reacting a compound of Formula V with an amine of the formula H$_2$N-R' wherein n, Z, R', and Q have the same meaning designated above in A.

C. Alkylating a compound of the formula

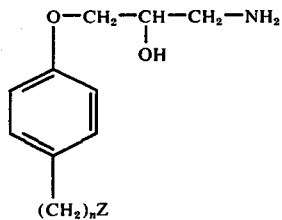
(VII)

reductively by using hydrogen and acetone to form a compound of the formula

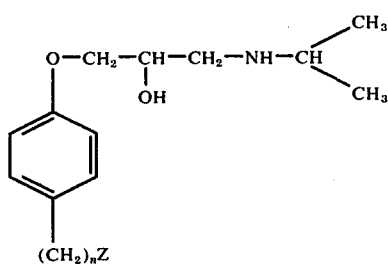
(VIII)

in which formulas n, and Z have the same meaning as designated in A.

D. Alkylating a compound of the formula

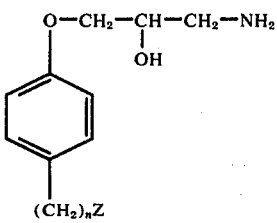
(IX)

by reacting it with a compound of the formula X-CH-[CH$_3$]$_2$ to form compounds of formula VIII, wherein n, Z, R', and X have the same meaning as designated in A.

E. Hydrolysis of a compound of the formula

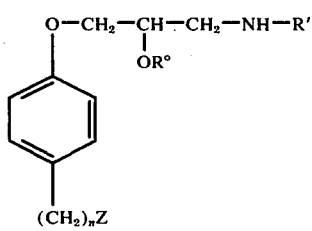
(X)

wherein n, Z, and R' have the same meaning as in A and R° is a group which can be removed hydrolytically, preferably an acyl or a tetrahydropyranyl group.

F. Hydrolysis of a compound of the formula

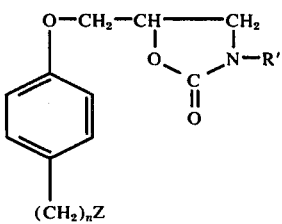
(XI)

using a strong alkali or strong acid, wherein n, Z, and R' have the same meaning as in A.

g. Hydrolysis or pyrolysis of a compound of the formula

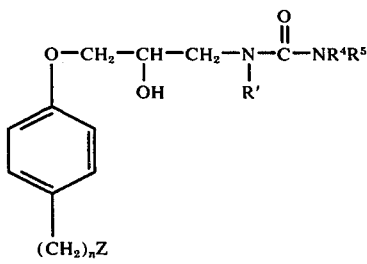
(XII)

wherein n, Z, and R' have the same meaning as above and R$^4$ and R$^5$ each represents a hydrogen atom, a lower alkyl, aralkyl, or aryl group.

H. Hydrolysis or hydrogenolysis of a compound of the formula

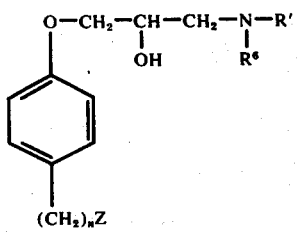

(XIII)

wherein n, Z, and R' have the same meaning as in A and $R^6$ is a protecting group such as a benzyl, acetyl or carbobenzoxy group.

I. Reacting a phenolate of the formula

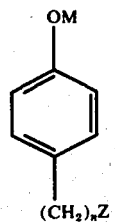

(XIV)

with a compound of the formula

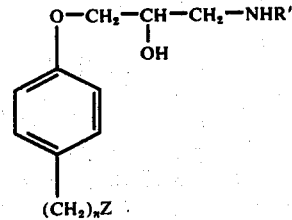

(IV)

in which formulas n, Z, R', and Q have the same meaning as in A and M is a cation, preferably an alkali metal action.

J. Reducing a compound of the formula

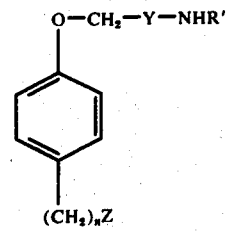

(XV)

preferably by using a complex alkali metal hydride, wherein n, Z, and R' have the same meaning as in A and Y represents -CHOH-CO- or -CO-$CH_2$-.

K. Hydrolysis of a compound of the formula

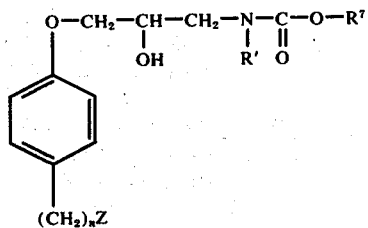

(XVI)

wherein n, Z, and R' have the same meaning as in A, and $R^7$ is a lower alkyl, aralkyl, or aryl group, preferably a phenyl group.

If desired, the racemates obtained by any of the methods A-K may be resolved into their optically active antipodes. When a pharmaceutically acceptable, non-toxic acid addition salt is desired, the compound formed is reacted with a suitable acid.

The method of preparation A is preferably performed in a high boiling, inert, organic solvent, such as 1,2,3,4-tetrahydronaphthalene, decahydronaphthalene, benzonitrile, paraffin oil or chlorinated, aromatic organic solvents; alternatively, the reaction may be carried out in the molten state at a temperature of 150° C. - 220° C., preferably 180° C. - 200° C.

The properties of the novel para-substituted phenoxyhydroxypropylamines, particularly their selectivity in blocking the β-receptors of the heart, make them useful in treating heart diseases in animals including humans. In clinical practice the compounds of the present invention will normally be administered orally, rectally or by injection, in the form of pharmaceutical preparations comprising as the active ingredient at least one of the compounds encompassed by Formula IV as defined herein. The active ingredients may be used either as a free base or as a pharmaceutically acceptable non-toxic, acid addition salt, for example, the hydrochloride, lactate, acetate, sulfamate, and the like, in association with a pharmaceutically acceptable carrier. Accordingly, terms relating to the novel compounds of this invention whether generically or specifically are intended to include both the free amine base and the acid addition salts of the free base, unless the context in which such terms are used, particularly in the examples, would be inconsistent with the broad concept. The carrier may be a solid, semi-solid or liquid diluent or capsule.

The pharmaceutical preparations are a further aspect of this invention. Usually the active substance will constitute between 0.1 and 95% by weight of the preparation, more specifically between 0.5 and 20% by weight for preparation intended for injection and between 0.2 and 50% by weight for preparations suitable for oral administration.

To produce pharmaceutical preparations containing a compound of the invention in the form of dosage units for oral application, the selected compound may be mxied with a solid pulverulent carrier, for example, lactose, saccharose, sorbitol, mannitol, starches such as potato starch, corn starch or amylopectin, cellulose derivatives, or gelatin, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, for example, gum arabic, gelatin, talcum, titanium dioxide, and the like.

Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatin capsules (pearl-shaped closed capsules) consisting of gelatin and, for example, glycerol or similar closed capsules, the active substance may be admixed with a vegetable oil. Hard gelatin capsules may contain granulates of the active substance in combination with solid, pulverulent carriers such as lactose, saccharose, sorbitol, mannitol, starches (e.g., potato starch, corn starch or amylopectin), cellulose derivatives or gelatin.

Dosage units for rectal application can be prepared in the form of suppositories comprising the active substance in admixture with a neutral fatty base, or gelatin rectal capsules comprising the active substance in admixture with vegetable oil or paraffin oil.

Liquid preparations for oral application may be in the form of syrups or suspensions, for example, solutions containing from about 0.2% to about 20% by weight of the active substance according to Formula IV, the balance being sugar and a mixture of ethanol, water, glycerol, and propylene glycol. Optionally, such liquid preparations may contain coloring agents, flavoring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to a about 10% by weight. These solutions may also contain stabilizing agents and/or buffering agents and may conveniently be provided in various dosage unit ampoules.

The following examples illustrate the principles and practices of the invention and are not intended to limit its scope in any way. All percentages are by weight unless otherwise indicated.

EXAMPLE I 1,2-epoxy-3-[p-(β-methoxyethyl)-phenoxyl]-propane (16.7 g) was dissolved in 50 ml isopropanol and mixed with 20 ml isopropylamine. The mixture was heated in an autoclave on boiling water-bath overnight, whereafter it was evaporated and the remainder dissolved in 2 N HCl. The solution was extracted first with ether and thereafter with methylene chloride. After evaporating the methylene chloride phase, the hydrochloride of 1-isopropylamino-3-[p-(β-methoxyethyl)-phenoxy]-propanol-2 was obtained which, after recrystallization from ethyl acetate, weighed 10.4 g. Melting point 83° C. Equiv. weight: found 304.0, calculated 303.8. The starting material 1,2-epoxy-3-[p-(β-methoxyethyl)-phenoxy]-propane was obtained from p-(β-methoxyethyl)-phenol which was reacted with epichlorohydrine whereafter the reaction product was distilled at 118°–128° C. at a pressure of 0.35 mm Hg.

According to the method described in Example I, the following compounds were similarly prepared as hydrochlorides.

EXAMPLE II 1-isopropylamino-3-[p-(β-ethoxyethyl)-phenoxy]-propanol-2. Melting point 102° C. Equiv. weight: found 323.0, calculated 317.8.

EXAMPLE III 1-isopropylamino-3-(p-ethoxymethyl-phenoxy)-propanol-2. Melting point 94° C. Equiv. weight: found 304.0, calculated 303.8.

EXAMPLE IV

1-Tertiarybutylamino-3-[p-(β-methoxyethyl)-phenoxy]-propanol-2 hydrochloride having the melting point 116° C was prepared in accordance with Example I except that the isopropyl amine was replaced by the tert.-butyl amine. Equivalent weight: found 319, calculated 318.

EXAMPLE V

1-Isopropylamino-3-[p-(β-methylmercaptoethyl)-phenoxy]-propanol-2 in base form was prepared in accordance with Example I with the exception that no reaction with hydrochloric acid took place. Melting point 60° C. Equivalent weight: found 284, calculated 283.

EXAMPLE VI

1-Isopropylamino-3-[p-(γ-methoxypropyl)-phenoxy]-propanol-2, melting point 89° C (hydrochloride) was prepared. The starting material p-(γ-methoxypropyl)-phenyl-glycidyl ether has a boiling point at 102°–112° C and 0.03 mm Hg. Equivalent weight: found 314.0, calculated 317.8.

EXAMPLE VII 1-isopropylamino-3-[p-(β-methoxycarbonylamidoethyl)-phenoxy]-propanol-2. Melting point 106° C. Equiv. weight: found 349, calculated 347.

EXAMPLE VIII 1-isopropylamino-3-[p-(β-ethoxycarbonylamidoethyl)-phenoxy]-propanol-2. Melting point 120° c. Equiv. weight: found 364, calculated 361.

The para-substituted phenylglycidyl ethers used in Examples II - VIII were obtained from the corresponding phenols and epichlorohydrin according to Example I. These glycidyl ethers were used without isolation until the last step.

EXAMPLE IX (Illustrating Method B)

5 g of p-(β-methoxyethyl)-phenol, 100 ml of epichlorhydrin and 0.5 ml of piperidine were heated on a boiling water bath for 10 hours. The mixture was thereafter evaporated at reduced pressure and the residue was dissolved in chloroform and was thereupon extracted with hydrochloric acid. The chloroform phase was washed with water, dried and evaporated at reduced pressure. The residue consisting of 3-[p-(β-methoxyethyl)-phenoxy]-1-chloropropanol-2 was dissolved in 20 ml of isopropyl alcohol to which was added 10 ml of isopropylamine and the mixture was heated in an autoclave on a water bath with boiling water for 10 hours. Thereafter the mixture was evaporated and the residue was shaken with a mixture of 2/N NaOH and ether. The ether phase was dried and evaporated at reduced pressure. The residue so obtained crystallized from petroleum ether and there was thus obtained 1-isopropylamino-3-[p-(β-methoxyethyl)-phenoxy]-propanol-2, which was converted to the hydrochloride in accordance with Example I. The melting point of the hydrochloride was 83° C.

EXAMPLE X (Illustrating Method C)

A solution of 20 g of p-(β-methoxyethyl)-phenyl glycidyl ether in 200 ml of ethanol saturated with ammonia was heated in an autoclave on a water bath with boiling water for 4 hours. The mixture was thereupon evaporated and the residue was dissolved in ethyl acetate whereupon gaseous HCl was introduced into the solution. The hydrochloride of the amine, which then crystallized, was removed by filtration and 5 g was dissolved in 50 ml of methanol and 10 ml off acetone. The solution was cooled to 0° C and 5 g of sodium borohydride was added in portions during 1 hour. Then 2.5 ml of acetone and 0.8 g of sodium borohydride were added and the solution was kept at room temperature for 1 hour whereupon 150 ml of $H_2O$ was added. The mixture was extracted with ether whereupon the ether phase was dried over potassium carbonate and evaporated. The residue was transformed to the hydrochloride by dissolving the base in ethyl acetate and introducing gaseous HCl into the solution. In this way the hydrochloride of 1-isopropylamino-3-[p-(β-methoxyethyl)-phenoxy]-propanol-2 was obtained having a melting point of 83° C.

EXAMPLE XI (Illustrating Method D)

A solution of 10 g of p-(β-ethoxyethyl)-phenyl glycidyl ether in 100 ml of ethanol was saturated with ammonia whereupon the mixture was heated upon a water bath containing boiling water for 4 hours. Thereafter the reaction mixture was evaporated and the residue dissolved in ethyl acetate. HCl in gaseous form was introduced causing the amine hydrochloride to crystallize. The crystals were removed by filtration and dissolved in 70 ml of ethanol whereupon 10 ml of isopropylbromide and 12 g of potassium carbonate was added. The mixture was heated in an autoclave at 120° C for 10 hours whereupon the ethanol was removed by evaporation. To the residue was added 100 ml of 2/N HCl and 100 ml of ether. The water phase was separated and alkalized with 2/N NaOH and thereupon extracted with ethyl acetate. The ethyl acetate phase was dried by means of potassium carbonate whereupon gaseous HCl was introduced. This caused crystallization of the hydrochloride which was separated by filtration and recrystallized from methylethylketone. There was thus obtained the hydrochloride of 1-isopropylamino-3-[p-(β-ethoxyethyl)-phenoxy]-propanol-2 having a melting point of 102° C.

EXAMPLE XII (Illustrating Method E)

A solution of 8 g of 3-[p-(β-ethoxyethyl)-phenoxy]-1-chloropropanol-2 (prepared for instance according to method B) in 15 ml of dihydropyran was mixed with a small amount of p-toluene sulphonic acid. This caused an increase of the temperature to 50° C and after having been kept at this temperature for 30 minutes the mixture was dissolved in 100 ml of ethanol whereupon 10 ml of isopropylamine was added. The reaction was heated in an autoclave for 10 hours on steam bath and was thererafter evaporated. The residue was dissolved in ethyl acetate to which was added oxalic acid and was thereupon diluted with ether. The crystallized oxalate was separated and recrystallized from ethanol/ether. To the oxalate was added 50 ml of 2/N HCl and the mixture was heated on water bath for 15 minutes. After cooling the mixture was alkalized by addition of NaOH and the base was extracted with ether. The ether phase was dried and evaporated whereafter the residue was dissolved in ethyl acetate followed by introduction of gaseous HCl. The precipitate thus obtained was recrystallized from methylethylketone which gave the hydrochloride of 1-isopropylamino-3-[p-(β-ethoxyethyl)-phenoxy]-propanol-2 having a melting point of 103° C.

EXAMPLE XIII (Illustrating Method F)

5.5 g of 3-isopropyl-5-[p-(β-methoxyethyl)-phenoxymethyl]-oxazolidinone-2 was dissolved in 60 ml of ethanol to which was added a solution of 9 g of KOH in 15 ml of $H_2O$. The mixture was refluxed, was thereupon evaporated and the residue dissolved in 2/N HCl and extracted with ether. The water phase was alkalized with NaOH and extracted with ether. After drying by means of potassium carbonate, gaseous HCl was introduced, causing the hydrochloride of 1-isopropylamino-3[p-(β-methoxyethyl)-phenoxy]-propanol-2 to crystallize. The hydrochloride gave after recrystallization from methylethyl ketone, a melting point of 83° C.

EXAMPLE XIV (Illustrating Method A and G)

4.5 g of p-(β-ethoxyethyl)-phenyl glycidyl ether was dissolved in 50 ml of tetralin to which was added 5.7 g of N,N'-diisopropylurea and 20 g of lithium hydroxide whereupon the mixture was heated at 200° C for 3 hours. The reaction mixture was after cooling diluted with 50 ml of ether and shaken with 100 ml of 2/N HCl. The water phase was extracted with ether and thereupon alkalized by addition of NaOH and was finally shaken with ether. The ether phase was washed with water, dried and evaporated. The residue was dissolved in ethyl acetate and the hydrocholoride precipitated by addition of a solution of gaseous HCl in ether. The hydrochloride of 1-isopropylamino-3-[p-(β-ethoxyethyl)-phenoxy]-propanol-2 with a melting point of 102° C was obtained after recyrstallization from methylethyl ketone.

EXAMPLE XV (Illustrating Method H and I)

0.92 g of Na was dissolved in 50 ml of alcohol and to the solution was added 6.1 g of p-(β-methoxyethyl)-phenol 9.6 g of 3-(N-benzyl-N-isopropylamino)-1-chloropropanol-2. The mixture was heated in an autoclave on steam bath overnight and was thereupon filter and evaporated to dryness. To the residue was added 100 ml of 2/N HCl and the mixture was extracted with ether whereupon the water phase was alkalized by addition of NaOH and thereupon shaken with ether. The ether phase was dried and evaporated and the residue obtained dissolved in 200 ml of alcohol and neutralized with concentrated HCl. To this solution was added 0.5 g of Pd/C catalyst and the reaction mixture was hydrogenated at atmospheric pressure until the calculated amount of $H_2$ had been consumed. After filtering, the reaction mixture was evaporated to dryness and the residue thereupon recrystallized from methylethylketone giving the hydrochloride of 1-isopropylamino-3-[p-($\beta$-methoxyethyl)-phenoxy]-propanol-2, having a melting point of 83° C.

EXAMPLE XVI

Illustrating Method J)

15.2 g of p-($\beta$-methoxyethyl)-phenol was dissolved in a solution of 4.6 g of Na in 100 ml of ethanol. To the solution was added 12.5 g of 2-hydroxy-3-chloropropionic acid and the mixture was refluxed for 3 hours. The mixture was thereupon evaporated and to the residue was added 100 ml of 2/N HCl and the resulting mixture was thereupon extracted with benzene. The benzene phase was shaken with sodium bicarbonate solution which was thereupon acidified by addition of HCl followed by an extraction with benzene. After evaporation 2-hydroxy-3-[p-(methoxyethyl-phenoxy]-propionic acid was obtained which was converted to N-isopropylamide by dissolving the acid in tetrahydrofuran followed by an addition of isopropylamine and dicyclohexyl-dicarbodiimide and heating the reaction mixture at 40° C for 5 hours. To the solution, after filtering, was added 5 g of lithium aluminum hydride and the mixture was refluxed overnight. After the application of conventional separation methods, 1-isopropylamino-3-[p-($\beta$-methoxyethyl)-phenoxy]-propanol-2 was obtained, which, after conversion to the hydrochloride, had a melting point of 82° C.

EXAMPLE XVII (Illustrating Method K)

To 5 g of N-isopropyl-N-[3-/p-($\beta$-methoxyethyl)-phenoxy]-2-hydroxypropyl] carbamic acid ethyl ester was added 25 ml of 2/N HCl and the mixture was heated on water bath for 2 hours. After cooling, the mixture was extracted with ether and the water phase was alkalized by addition of NaOH, followed by an extraction with ether. After drying and evaporation and recrystallization from petroleum ether, 1-isopropylamino-3-[p-($\beta$-methoxyethyl)-phenoxy]-propanol-2 was obtained having a melting point of 83° C, (hydrochloride).

EXAMPLE XVIII

1-Isopropylamino-3-[p-($\gamma$-aminopropyl)-phenoxy]-propanol-2-di-HCl (3.4 g) was dissolved in 15 ml H$_2$O. Sodium bicarbonate (2.6 g) was added to the solution and after a few minutes while stirring, 1.0 g of methyl chloroformate was added. The mixture was stirred overnight at room temperature, followed by extraction with methylene dichloride. The methylene dichloride phase was dried with K$_2$CO$_3$, filtered and evaporated. In this way the base form of 1-isopropylamino-3-[p-($\gamma$-methoxycarbonylamidopropyl)-phenoxy]-propanol-2- was obtained (m.p.=72° C). Equivalent weight: Found 329; Calculated 324.

The starting material, 1-isopropylamino-3-[p-($\gamma$-aminopropyl)-phenoxy]-propanol-2, was prepared in the following manner: p-($\beta$-cyanoethyl)phenol (100.9 g), 149.1 g epichlorohydrin, 226 g K$_2$CO$_3$ and 700 ml acetonitrile were mixed and refluxed while stirring overnight.

After filtration, the filtrate was evaporated in vacuo. The residue (115 g) was dissolved in 300 ml of isopropanol; 300 ml of isopropylamine was added, whereupon the mixture ws refluxed for 3 hours. After evaporation in vacuo 138.5 g of an oil was obtained. 8.5 g of this oil was dissolved in 500 ml of ethanol (99%) and 8.5 ml of conc. HCl was added, followed by hydrogenation at 3.5 atm. (0.5 g. Pd/C as a catalyzing agent) until the calculated amount of hydrogen was consumed. After filtration, evaporation and recrystallization from alcohol, the dihydrochloride of 1-isopropylamino-3-[p-($\gamma$-aminopropyl)-phenoxy]-propanol-2 (m.p. 180° C) was obtained.

EXAMPLE XIX

According to the method described in Example XVIII the compound 1-tert.-butylamino-3[p-($\beta$-methoxycarbonylamidoethyl)-phenoxy]-propanol-2 was prepared (m.p.=92° C in base form; Equivalent weight: found 325; calculated 324). The compound -1-tert.-butylamino-3-[p-($\beta$-aminoethyl)-phenoxy]-propanol-2-di-HCl (m.p.=192° C) was used as starting material. This latter compound was prepared according to the method described in Example XVIII using p-cyanomethylphenol and tert.-butylamine as starting materials.

PHARMACOLOGICAL EVALUATION

Compounds prepared according to the examples were evaluated for intrinsic activity and blocking effect on heart rate and: peripheral vasodilator response to isoprenaline in the cat. The acute LD$_{50}$ in mice was evaluated. Alprenolol was used as a reference substance.

Cats weighing between 1.8 and 2.8 kg were anaesthetized with 30 mg/kg pentobarbital sodium, intraperitoneally. The cats had been pretreated with reserpine, 5 mg/kg intramuscular, about 18 hours before the experiment. Bilateral vagotomy was performed before the start of the experiment.

The heart rate was recorded on an Offner cardiotachometer triggered by the EKG-complex. Mean arterial blood pressure was recorded from a carotid artery. The peripheral resistance was measured in one of the legs of the cat in the following way: The femoral artery was opened in the inguinal region and the leg was perfused by blood delivered through a sigma motor pump at constant rate. The flow resistance (the pressure) was recorded via a pressure transudcer connected to the catheter distally to the pump. The paw was excluded from the circulation by a tight ligature Intravenously injected isoprenaline increased the heart rate and reduced the perfusion pressure. An isoprenaline dose giving 70–80% of the maximal chronotropic response was determined. This dose (usually 0.1 $\mu$g/kg) was then repeated with 20 minute intervals. Ten minutes before each isoprenaline injection, the tested substances were administered intravenously for two minutes, starting with a dose of 0.01 mg/kg and increasing each subsequent dose fourfold. The intrinsic effects of the test substances were determined. The dose producing 50% blockade of the isoprenaline responses was evaluated from the plotted log dose-percent blockade diagrams.

Table I shows the results of the foregoing experiments for intrinsic stimulating activity on heart rate in cats, $\beta$-blocking activity on heart rate and peripheral vascular resistance in cats and LD$_{50}$ after intraperitoneal administration in mice.

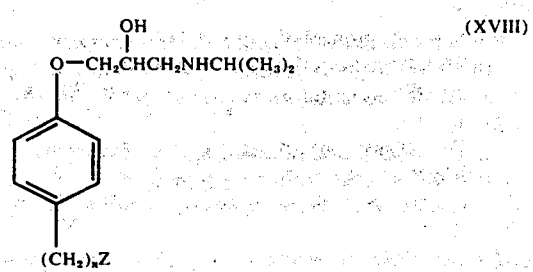

(XVIII)

TABLE I

| Compounds Tested | Reserpinized cat | | | Mouse |
| --- | --- | --- | --- | --- |
| $(CH_2)_nZ$ (except allyl) | Intrinsic activity % of maximal isoprenaline heart rate | β-blockade Heart rate $ED_{50}$ mg/kg | β-blockade peripheral vascular resistance $ED_{50}$ mg/kg | $LD_{50}$ i.p. mg/kg |
| o-allyl (alprenolol) | 20 | 0.1 | 0.05 | 100 |
| $CH_3OCH_2CH_2$—(Ex. I) | 0 | 0.4 | 3 | 200 |
| $C_2H_5OCH_2CH_2$—(Ex. II) | 0 | 0.3 | 4 | 150 |
| $C_2H_5OCH_2$—(Ex. III) | 0 | 0.4 | 6 | 175 |
| $CH_3OC\underset{\underset{O}{\|\|}}{}-NHCH_2CH_2-$ (Ex. VII) | 0 | 0.4 | 19 | 125 |
| $C_2H_5OC\underset{\underset{O}{\|\|}}{}-NHCH_2CH_2-$ (Ex. VIII) | 0 | 0.3 | 25 | 200 |

The results reported in Table I, show that the phenoxy-hydroxypropylamine test substances according to the invention were 3–4 times less active than alprenolol, the standard reference, as regards blockade of the β-receptors of the heart. The peripheral vascular β-blocking activity for the test substances was 60–500 times lower than the activity of alprenolol. These results demonstrate that the test substances, developed a relatively stronger blockade of the β-receptors of the heart than of the receptors in smooth muscles. Due to this cardioselectivity, the compounds according to the invention give therapeutic effects in treating cardiovascular diseases without risk or complications due to β-blockade in bronchi and blood vessels.

The following examples illustrate methods of preparing some pharmaceutical preparations according to the invention.

EXAMPLE XX

A syrup containing 2% (weight per volume) of active substance according to the invention was produced from the following ingredients:

| | |
| --- | --- |
| 1-isopropylamino-3-(p-methoxyethyl-phenoxy) propanol-2 [HCl] | 2.0 g |
| Saccharin | 0.6 g |
| Sugar | 30.0 g |
| Glycerol | 5.0 g |
| Flavoring agent | 0.1 g |
| Ethanol (96%) | 10.0 ml |
| Distilled water (balance) | to 100.0 ml |

The sugar, saccharin and the ether salt were dissolved in 60 grams of hot water. After cooling, the glycerol was added and a solution of the flavoring agent in ethanol was added. The mixture was then made up to a volume of 100 milliliters with water.

The active substance in this composition may be replaced by other pharmaceutically acceptable, nontoxic acid addition salts.

EXAMPLE XXI 1-isopropylamino-3-(p-ethoxyethylphenoxy)-propanol-2 hydrochloride (250 g) was mixed with lactose (175.8 g), potato starch (169.7 g) and collodial silica (32 g). The mixture was moistened with a 10% gelatin solution and granulated through a 12 mesh sieve. After drying, potato starch (160 g), talc (50 g) and magnesium stearate (2.5 g) were mixed in and the resulting mixture was pressed into tablets (10,000) containing 25 milligrams of active substance which were suitable for use as tablets. The tablets were marked with break lines to enable a dose other than 25 miligrams or multiples thereof to be administered.

EXAMPLE XXII

A granulate was prepared from 1-isopropylamino-3-(ethoxymethyl-phenoxy)-propanol-2 hydrochloride (250 g), lactose (175.9 g) and an alcoholic solution of polyvinyl pyrrolidone (25 g). After drying, the granulate was mixed with talc (25 g), potato starch (40 g) and magnesium stearate (2.50 g) and pressed into 10,000 biconvex tablets. These tablets were first coated with a 10% alcoholic shellac solution and then with a water solution containing saccharose (45%), gum arabic (5%), gelatin (4%) and dyestuff (0.2%). Talc and sugar powder were used as dusting powders after the first 15 applications. The coating was then finished with a 66% sugar syrup and polished with a 10% carnauba wax solution in carbon tetrachloride.

EXAMPLE XXIII 1-isopropylamino-3-(p-methoxyethylphenoxy)-propanol-2 hydrochloride (1 g), sodium chloride (0.8 g) and ascorbic acid (0.1 g) were dissolved in sufficient distilled water to make 100 milliliters of solution. This solution, each milliliter of which contained 10 milligrams of the active substance, was used to fill ampoules which were sterilized by heating for 20 minutes at 120° C.

Many obvious variations of the invention disclosed will suggest themselves to those skilled in the art. Nothing in the preceding specification is intended, however, to limit the scope of the invention as defined by the following claims.

We claim:
1. A compound of the formula

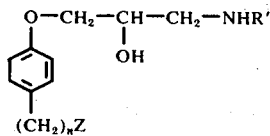

and pharmaceutically acceptable, non-toxic acid addition salts thereof, wherein R' is an isopropyl or tertiary butyl radical; Z is a member selected from the group consisting of -OR", and -SR", R" being a straight or branched alkyl radical having 1 to 3 carbon atoms; and n is 1, 2, or 3.

2. A compound according to claim 1 in racemic form and pharmaceutically acceptable, non-toxic acid addition salts thereof.

3. A compound according to claim 1 resolved into its optically active, levo-rotatory isomers and pharmaceutically acceptable, non-toxic acid addition salts thereof.

4. A compound according to claim 1 resolved into its optically active, dextro-rotatory isomer and pharmaceutically acceptable, non-toxic acid addition salts thereof.

5. A compound according to claim 1 wherein R' is isopropyl.

6. A compound according to claim 1 wherein Z is -OR".

7. A compound according to claim 1 wherein Z is -SR".

8. A compound according to claim 5 wherein Z is -OR" or -SR".

9. The compound of claim 1 (±)-1-isopropylamino-3-[p-(β-methoxyethylphenoxy]-propanol-2 and pharmaceutically acceptable, non-toxic acid addition salts thereof.

10. The compound of claim 1 (−)-1-isopropylamino-3-[p-(β-methoxyethylphenoxy]-propanol-2 and pharmaceutically acceptable, non-toxic acid addition salts thereof.

11. The compound of claim 1 (+0-1-isopropylamino-3-[p-(β-methoxyethylphenoxy]-propanol-2 and pharmaceutically acceptable, non-toxic acid addition salts thereof.

12. The compound of claim 1 (±)-1-isopropylamino-3-[p-(β-ethoxyethyl)-phenoxy]-propanol-2 and pharmaceutically acceptable, non-toxic acid addition salts thereof.

13. The compound of claim 1 (−)-1-isopropylamino-3-[p-(β-ethoxyethyl)-phenoxy]-propanol-2 and pharmaceutically acceptable, non-toxic acid addition salts thereof.

14. The compound of claim 1 (+)-1-isopropylamino-3-[p-(β-ethoxyethyl)-phenoxy]-propanol-2 and pharmaceutically acceptable, non-toxic acid addition salts thereof.

15. The compound of claim 1 (±)-1-isopropylamino-3-[p-(ethoxymethyl)-phenoxy]-propanol-2 and pharmaceutically acceptable, non-toxic acid addition salts thereof.

16. The compound of claim 1 (−)-1-isopropylamino-3-[p-(ethoxymethyl)-phenoxy]-propanol-2 and pharmaceutically acceptable, non-toxic acid addition salts thereof.

17. The compound of claim 1 (+)-1-isopropylamino-3-[p-ethoxymethyl)-phenoxy]-propanol-2 and pharmaceutically acceptable, non-toxic acid addition salts thereof.

18. The compound of claim 1 wherein R' is tert.-butyl.

19. The compound of claim 1 (±)-1-isopropylamino-3-[p-(β-methylmercaptoethyl)-phenoxy]-propanol-2 and pharmaceutically acceptable, non-toxic acid addition salts thereof.

20. The compoud of claim 1 (±)-1-isopropylamino-3-[p-(γ-methoxypropyl)-phenoxy]-propanol-2 and pharmaceutically acceptable, non-toxic acid addition salts thereof.

* * * * *

UNITED STATES PATENT OFFICE
CERTIFICATE OF CORRECTION

Patent No. 3,998,790  Dated December 21, 1976

Inventor(s) Arne Elof Brändstrom et al.

It is certified that error appears in the above-identified patent and that said Letters Patent are hereby corrected as shown below:

Column 16, line 3, "(+0-1-" should read -- (+)-1- --.

Column 16, line 37, "compoud" should read -- compound --.

Signed and Sealed this

Seventeenth Day of October 1978

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 3,998,790
DATED : December 21, 1976
INVENTOR(S) : Arne Elof Brandstrom et al.

It is certified that error appears in the above-identified patent and that said Letters Patent are hereby corrected as shown below:

Front Page, insert the following Item after Item [60]:

-- [30]     Foreign Application Priority Data

Feb. 18, 1970    Sweden . . . . . 2050/70 --

Signed and Sealed this

Twenty-seventh Day of February 1979

[SEAL]

Attest:

RUTH C. MASON
*Attesting Officer*

DONALD W. BANNER
*Commissioner of Patents and Trademarks*

UNITED STATES PATENT AND TRADEMARK OFFICE

CERTIFICATE EXTENDING PATENT TERM
UNDER 35 U.S.C. § 156

PATENT NO.:      3,998,790

DATED:           December 21, 1976

INVENTORS:       Arne Elof Brandstrom et al.

PATENT OWNER:    Aktiebolaget Hassle

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks